United States Patent [19]

Gaughan

[11] 4,088,687
[45] May 9, 1978

[54] HERBICIDAL ACTIVE CARBOXANILIDE DERIVATIVE

[75] Inventor: Edmund J. Gaughan, Berkeley, Calif.

[73] Assignee: Stauffer Chemical Company, Westport, Conn.

[21] Appl. No.: 655,651

[22] Filed: Feb. 6, 1976

Related U.S. Application Data

[60] Division of Ser. No. 539,200, Jan. 6, 1975, which is a continuation-in-part of Ser. No. 449,782, Mar. 11, 1974, abandoned, which is a continuation-in-part of Ser. No. 360,242, May 14, 1973, abandoned.

[51] Int. Cl.² .................................... C07C 103/37
[52] U.S. Cl. .................. 260/557 R; 260/340.5 R; 260/347.3; 260/558 R; 260/562 R; 424/324
[58] Field of Search .................................... 260/557 R

[56] References Cited

U.S. PATENT DOCUMENTS

| | | | |
|---|---|---|---|
| 3,100,205 | 8/1963 | Schulte et al. | 260/557 R |
| 3,201,466 | 8/1965 | Dubrovin | 260/557 R |
| 3,277,107 | 10/1966 | Neighbors | 260/557 R |
| 3,407,056 | 10/1968 | Schwartz | 71/118 |
| 3,484,485 | 12/1969 | Schwartz | 260/557 R |
| 3,852,058 | 12/1974 | Huffman | 71/118 |

OTHER PUBLICATIONS

Chem. Abstracts 82:72769y.

*Primary Examiner*—Ethel G. Love
*Attorney, Agent, or Firm*—Daniel C. Block

[57] ABSTRACT

This invention relates to herbicidal active compounds and their use. The compounds of this invention correspond to the formula:

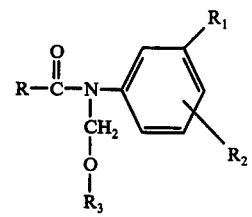

wherein R is selected from cyclopropyl, ethyl, furyl, benzyl, methyl, and 3,4-methylenedioxybenzyl; $R_1$ is selected from chloro and trifluoromethyl; $R_2$ is selected from hydrogen, 4-chloro, 4-propargyloxy, and 5-chloro; $R_3$ is selected from ethyl, chloroethyl, isobutyl, allyl and propargyl.

9 Claims, No Drawings

HERBICIDAL ACTIVE CARBOXANILIDE DERIVATIVE

CROSS REFERENCE TO RELATED APPLICATION

This is a division of continuation-in-part application Ser. No. 539,200, filed Jan. 6, 1975 which in turn is a continuation-in-part of copending application, Ser. No. 449,782, filed Mar. 11, 1974, now abandoned which is a continuation-in-part of application Ser. No. 360,242 filed May 14, 1973, now abandoned.

DESCRIPTION OF THE INVENTION

This invention relates to a group of compounds that have unusual herbicidal activity. The compounds are represented by the formula:

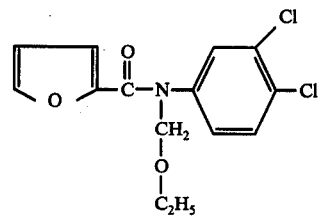

wherein R is selected from cyclopropyl, ethyl, furyl, benzyl, methyl, and 3,4-methylenedioxy-benzyl; $R_1$ is selected from chloro and trifluoromethyl; $R_2$ is selected from hydrogen, 4-chloro, 4-propargyloxy, and 5-chloro; $R_3$ is selected from ethyl, chloroethyl, isobutyl, allyl and propargyl.

In general, the compounds of this invention are made by reacting a salt of an appropriate carboxanilide with an appropriate haloalkyl ether in an inert solvent. The end product is separated in good yields.

In order to illustrate the merits of the invention, the following examples are provided:

EXAMPLE 1

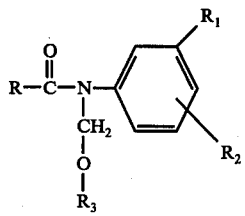

The sodium salt of cyclopropane-3',4'-dichlorocarboxanilide was formed by reacting 6.9 g. (0.03 moles) of the carboxanilide with 0.8 g. (0.032 moles) of sodium hydride in 70 ml. of tetrahydrofuran. Then, 3.0 g. (0.032 moles) of chloromethyl ethylether in 5 ml. of tetrahydrofuran were added. Heat was evolved and a precipitate appeared. The mixture was then warmed to 50°–55° C. for 1 hour. It was then cooled and filtered. The solvent was removed in vacuo and the residue taken up in benzene. The solution was washed with sodium bicarbonate, dried and the benzene removed in vacuo to yield 5.6 g. of product.

EXAMPLE 2

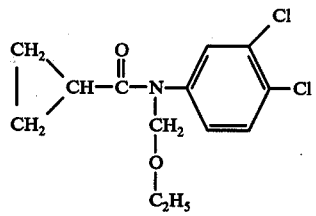

To a suspension of 0.8 g. (.032 moles) of sodim hydride in 15 ml. of dry tetrahydrofuran was added a solution of 7.7 g. (0.03 moles) of 3',4'-dichlorofuranilide in 65 ml. of the same solvent at room temperature. The mixture was stirred ½ hour at room temperature, ½ hour at 40°–45°, and cooled to room temperature. The ether in 5 ml. of tetrahydrofuran was added, and a precipitate of sodium chloride formed. The mixture was stirred 1 hour at room temperature and 1 hour at 50°–55°. It was cooled, filtered through Celite, and evaporated in vacuo. The residue was taken up in benzene, washed with 5% sodium bicarbonate solution, and the organic phase dried over magnesium sulfate. Removal of the solvent left the product as a semi-solid. Yield: 6.1 g. (65%).

EXAMPLE 3

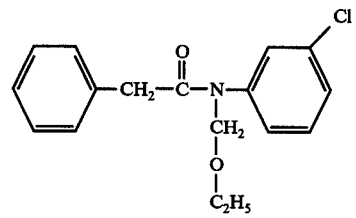

The reaction was carried out and the product worked up as in Example 2 above. The reactants were 7.4 g. (0.03 moles) of 2-phenyl-3'-chloroacetanilide, 0.8 g. (0.032 moles) of sodium hydride, and 3.0 g. (0.032 moles) of chloromethyl ethyl ether. The product was a viscous yellow oil. Yield: 6.0 g. (69%). The structure was confirmed by IR spectroscopy.

EXAMPLE 4

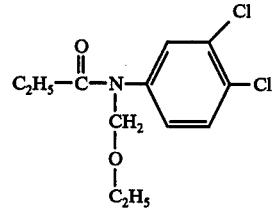

To a suspension of 0.8 g. (0.032 moles) of sodium hydride in 10 ml. of dry tetrahydrofuran was added a solution of 6.5 g. (0.03 moles) of 3',4'-dichloropropionanilide in 65 ml. of the same solvent at room temperature. Hydrogen was evolved. The mixture was stirred ½ hour at room temperature and ½ hour at 40°–45°. It was cooled to room temperature and 3.0 g. (0.032 moles) of chloromethyl ethyl ether in 5 ml. of tetrahydrofuran added all at once. The temperature rose to about 38° and a precipitate of sodium chloride appeared. The mixture was stirred 1 hour at room temperature and 1 hour at 50°-55°. After cooling, it was filtered through Celite and the solvent removed in vacuo. The residual oil was taken up in benzene, refiltered and again evaporated, finally under 0.5 mm. vacuum. The product was a colorless oil. Yield: 5.7 g. (69%). This compound could be distilled in vacuo, b. p. 123°-126°/0.05 mm. Its structure was confirmed by IR and NMR spectroscopy.

EXAMPLE 5

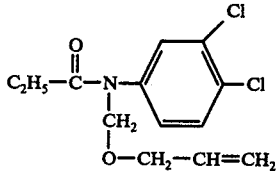

The reaction was carried out and the product worked up as in Example 2. The reactants were 6.5 g. of 3',4'-dichloropropionanilide, 0.8 g. (0.032 moles) of sodium hydride, and 3.4 g. (0.032 moles) of chloromethyl allyl ether. The product was a yellow oil. Yield: 5.5 g. (64%). Its structure was confirmed by IR spectroscopy.

Other compounds were prepared in an analogous manner starting with the appropriate starting materials as outlined above. The following table of compounds is representative of those embodied by the present invention. Compound numbers have been assigned to them and are used for identification throughout the balance of the specification.

TABLE I

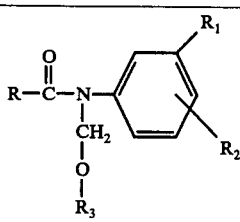

| Compound No. | R | $R_1$ | $R_2$ | $R_3$ |
| --- | --- | --- | --- | --- |
| 1 | -CH(CH₂)₂ (cyclopropyl) | —Cl | 4-Cl | —C₂H₅ |
| 2 | —C₂H₅ | —CF₃ | 4-Cl | —C₂H₅ |
| 3 | -CH(CH₂)₂ (cyclopropyl) | —CF₃ | 4-Cl | —C₂H₅ |
| 4 | -CH(CH₂)₂ (cyclopropyl) | —Cl | 4-O—CH₂—C≡CH | —C₂H₅ |
| 5 | 2-furyl | —Cl | 4-Cl | —C₂H₅ |
| 6 | 2-furyl | —CF₃ | H | —C₂H₅ |
| 7 | 2-furyl | —Cl | -5-Cl | —C₂H₅ |
| 8 | —CH₂—C₆H₅ | —Cl | H | —C₂H₅ |
| 9 | —CH₂—C₆H₅ | —Cl | 4-Cl | —C₂H₅ |

TABLE I-continued $$R-\underset{\underset{\underset{R_3}{O}}{\underset{|}{CH_2}}}{\overset{O}{\overset{\|}{C}}}-N-\underset{R_2}{\overset{R_1}{\bigcirc}}$$

| Compound No. | R | $R_1$ | $R_2$ | $R_3$ |
|---|---|---|---|---|
| 10 | -CH(CH$_2$)(CH$_2$) (cyclopropyl) | -Cl | 4-Cl | -CH$_2$-CH(CH$_3$)$_2$ |
| 11 | -CH(CH$_2$)(CH$_2$) (cyclopropyl) | -Cl | -5-Cl | -C$_2$H$_5$ |
| 12 | -C$_2$H$_5$ | -Cl | 4-Cl | -C$_2$H$_5$ |
| 13 | -CH$_3$ | -Cl | 4-Cl | -C$_2$H$_5$ |
| 14 | -CH(CH$_2$)(CH$_2$) (cyclopropyl) | -Cl | 4-Cl | -C$_2$H$_4$Cl |
| 15 | -CH$_2$-(3,4-methylenedioxyphenyl-like, benzodioxole) | -Cl | 4-Cl | -C$_2$H$_5$ |
| 16 | -CH$_3$ | -Cl | 4-O-CH$_2$-C≡CH | -C$_2$H$_5$ |
| 17 | -C$_2$H$_5$ | -Cl | 4-O-CH$_2$-C≡CH | -C$_2$H$_5$ |
| 18 | -C$_2$H$_5$ | -Cl | 4-Cl | -CH$_2$-CH=CH$_2$ |
| 19 | -CH(CH$_2$)(CH$_2$) (cyclopropyl) | -Cl | 4-Cl | -CH$_2$-CH=CH$_2$ |
| 20 | -CH(CH$_2$)(CH$_2$) (cyclopropyl) | -Cl | 4-Cl | -CH$_2$-CH≡CH |

All of the above compounds were identified by standard analytical procedures using IR spectroscopy and/or NMR spectroscopy.

Herbicidal Screening Tests

As previously mentioned, the novel compounds herein described are phytotoxic compounds which are useful and valuable in controlling various plant species. The compounds of this invention are tested as a herbicide in the following manner.

A. Preemergence Herbicide Screening Test: Using an analytical balance, 20 mg. of the compound to be tested is weighed out on a piece of glassine weighing paper. The paper and compound are placed in a 30 ml. widemouth bottle and 3 ml. of acetone containing 1% Tween 20 ® is added to dissolve the compound. If the material is not soluble in acetone, another solvent such as water, alcohol or dimethylformamide (DMF) is used instead. When DMF is used, only 0.5 ml. or less is used to dissolve the compound and then another solvent is used to make the volume up to 3 ml. The 3 ml. of solution is sprayed uniformly on the soil contained in a small styrofoam flat one day after planting weed seeds in the flat of soil. A No. 152 DeVilbiss atomizer is used to apply the spray using compressed air at a pressure of 5 lb/sq. in. The rate of application is 8 lb./acre and the spray volume is 143 gal./acre.

On the last day preceding treatment, the styrofoam flat, which is 7 inches long, 5 inches wide and 2.75 inches deep, is filled to a depth of 2 inches with loamy sand soil. Seeds of seven different weed species are planted in individual rows using one species per row across the width of the flat. The seeds are covered with soil so that they are planted at a depth of 0.5 inch. The seeds used are hairy crabgrass (*Digitaria sanguinalis*), yellow foxtail (*Setaria glauca*), watergrass (*Echinochloa crusgalli*), red oat (*Avena sativa*), redroot pigweed (*Amaranthus retroflexus*), Indian mustard (*Brassica juncea*) and curly dock (*Rumex crispus*). Ample seeds are planted to give about 20 to 50 seedlings per row after emergence depending on the size of the plants.

After treatment, the flats are placed in the greenhouse at a temperature of 70° to 85° F. and watered by sprinkling. Two weeks after treatment the degree of injury or control is determined by comparison with untreated check plants of the same age. The injury rating from 0 to 100% is recorded for each species as percent control with 0% representing no injury and 100% representing complete kill.

B. Postemergence Herbicide Screening Test: Seeds of six plant species, including hairy crabgrass, watergrass, red oat, mustard, curly dock and Pinto beans (*Phaseolus vulgaris*) are planted in the styrofoam flats as described above for preemergence screening. The flats are placed in the greenhouse at 70° to 85° F. and watered daily with a sprinkler. About 10 to 14 days after planting when the primary leaves of the bean plants are almost fully expanded and the first trifoliate leaves are just starting to form, the plants are sprayed. The spray is prepared by weighing out 20 mg. of the test compound, dissolving it in 5 ml. of acetone containing 1% Tween 20 ® and then adding 5 ml. of water. The solution is sprayed on the foliage using a No. 152 DeVilbiss atomizer at an air pressure of 5 lb./sq. in. The spray concentration is 0.2% and the rate is 8 lb./acre. The spray volume is 476 gal./acre.

Injury ratings are recorded 14 days after treatment. The rating system is the same as described above for the pre-emergence test. The results of these tests are recorded in Table II.

TABLE II

| Compound No. | Pre-emergent | Post-emergent |
|---|---|---|
| 1 | 100 | 100 |
| 2 | 92 | 77 |
| 3 | 94 | 100 |
| 4 | 97 | 100 |
| 5 | 37 | 68 |
| 6 | 23 | 7 |
| 7 | 34 | 75 |
| 8 | 57 | 77 |
| 9 | 91 | 93 |
| 10 | 75 | 99 |
| 11 | 95 | 97 |
| 12 | 99 | 99.8 |
| 13 | 60 | 82 |
| 14 | 100 | 100 |
| 15 | 74 | 70 |
| 16 | 71 | 97 |
| 17 | 99.7 | 97 |
| 18 | 50 | 100 |
| 19 | 75 | 100 |
| 20 | 80 | 100 |

It has been found in practice that the compounds of this invention function in a completely different and unusual manner. When using the compounds of this invention as a pre-emergent herbicide, the weed seeds germinated and sprouted. When they emerged through the soil surface, they were devoid of any green color and appeared to be bleached. When using the compounds of this invention as a post-emergent herbicide, the green color in the weed species soon faded and took on a bleached appearance. In view of these findings, it has been concluded that the compounds of this invention function to inhibit the formation of chlorophylls and carotenes in the weed species. This bleaching characteristic is not observed in other closely related herbicidal active compounds.

The compounds of the present invention are used as pre-emergence or post-emergence herbicides and are applied in a variety of ways at various concentrations. In practice, the compounds are formulated with an inert carrier, utilizing methods well-known to those skilled in the art, therby making them suitable for application as dusts, sprays, or drenches and the like, in the form and manner required. The mixtures can be dispersed in water with the aid of a wetting agent or they can be employed in organic liquid compositions, oil and water, water in oil emulsions, with or without the addition of wetting, dispersing or emulsifying agents. An herbicidally effective amount depends upon the nature of the seeds or plants to be controlled and the rate of application varies from 0.1 to approximately 50 pounds per acre.

The phytotoxic compositions of this invention employing an herbicidally effective amount of the compound described herein are applied to the plants in the conventional manner. Thus, the dust and liquid compositions can be applied to the plant by the use of power-dusters, boom and hand sprayers and spray-dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles and these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The concentration of a compound of the present invention, constituting an effective amount in the best mode of administration in the utility disclosed, is readily determinable by those skilled in the art.

Various changes and modifications are possible without departing from the spirit and scope of the invention described herein and will be apparent to those skilled in the art to which it pertains. It is accordingly intended that the present invention shall only be limited by the scope of the claims.

What is claimed is:

1. A compound corresponding to the formula:

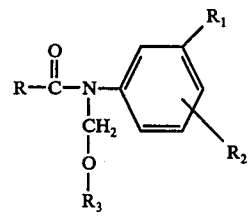

wherein R is cyclopropyl; $R_1$ is selected from chloro and trifluoromethyl; $R_2$ is selected from 4-chloro, 4-propargyloxy, and 5-chloro; $R_3$ is selected from ethyl, chloroethyl, isobutyl, allyl, and propargyl.

2. The compound of claim 1 wherein R is cyclopropyl, $R_1$ is chloro, $R_2$ is 4-chloro and $R_3$ is ethyl.

3. The compound of claim 1 wherein R is cyclopropyl, $R_1$ is trifluoromethyl, $R_2$ is 4-chloro and $R_3$ is ethyl.

4. The compound of claim 1 wherein R is cyclopropyl, $R_1$ is chloro, $R_2$ is 4-propargyloxy and $R_3$ is ethyl.

5. The compound of claim 1 wherein R is cyclopropyl, $R_1$ is chloro, $R_2$ is 4-chloro and $R_3$ is isobutyl.

6. The compound of claim 1 wherein R is cyclopropyl, $R_1$ is chloro, $R_2$ is 5-chloro and $R_3$ is ethyl.

7. The compound of claim 1 wherein R is cyclopropyl, $R_1$ is chloro, $R_2$ is 4-chloro and $R_3$ is chloroethyl.

8. The compound of claim 1 wherein R is cyclopropyl, $R_1$ is chloro, $R_2$ is 4-chloro and $R_3$ is allyl.

9. The compound of claim 1 wherein R is cyclopropyl, $R_1$ is chloro, $R_2$ is 4-chloro and $R_3$ is propargyl.

* * * * *